United States Patent
Asakura et al.

(10) Patent No.: US 6,777,212 B2
(45) Date of Patent: Aug. 17, 2004

(54) MICROBIAL PROCESS FOR PRODUCING L-ASCORBIC ACID, D-ERYTHORBIC ACID, AND SALTS THEREOF

(75) Inventors: Akira Asakura, Fujisawa (JP); Tatsuo Hoshino, Kamakura (JP); Masako Shinjoh, Kamakura (JP)

(73) Assignee: Roche Vitamins, Inc., Parsippany, NJ (US)

( * ) Notice: Subject to any disclaimer, the term of this patent is extended or adjusted under 35 U.S.C. 154(b) by 246 days.

(21) Appl. No.: 09/938,035

(22) Filed: Aug. 23, 2001

(65) Prior Publication Data

US 2003/0105160 A1 Jun. 5, 2003

(30) Foreign Application Priority Data

Aug. 23, 2000 (EP) ............................... 00118059

(51) Int. Cl.[7] .............................. C12P 17/04; C12P 7/58; C12N 1/20
(52) U.S. Cl. ...................... 435/126; 435/187; 435/252.1
(58) Field of Search ................. 435/126, 137, 435/252.1

(56) References Cited

U.S. PATENT DOCUMENTS 5,817,490 A * 10/1998 Hubbs ........................ 435/137
6,146,860 A * 11/2000 Asakura et al. ............. 435/126
6,358,715 B1 * 3/2002 Kumar ....................... 435/138

FOREIGN PATENT DOCUMENTS

EP 1026257 * 1/2000
EP 1 026 257 A1 8/2000
WO WO 97/43433 11/1997

OTHER PUBLICATIONS

Hiraiashi, et al., "Phylogenetic characterization of a new thermoacidophilic bacterium isolated from hot springs in Japan," *J. Gen. Appl. Microbiol.*, vol. 43, pp. 295–304 (1997).

Wisotzkey, et al., "Comparative Sequence Analyses on the 16S rRNA (rDNA) of *Bacillus acidocaldarius, Bacillus acidoterrestris*, and *Bacillus cycloheptanicus* and Proposal for Creation of a New Genus, *Alicyclobacillus* gen. Nov.," *International Journal of Systematic Bacteriology*, vol. 42, No. 2, pp. 263–269 (1992).

Albuquerque, et al., "*Alicyclobacillus hesperidum* sp. nov, and a related genomic species from solfatario soils of Sao Miguel in the Azores," *International Journal of Systematic and Evolutionary Microbiology*, vol. 50, pp. 451–457 (2000).

* cited by examiner

Primary Examiner—Dr. Herbert J. Lilling
(74) Attorney, Agent, or Firm—Bryan Cave LLP

(57) ABSTRACT

A process for producing L-ascorbic acid or D-erythorbic acid, or in each case its sodium, potassium or calcium salt, from 2-keto-L-gulonic acid or 2-keto-D-gluconic acid, or in each case its sodium, potassium or calcium salt, that involves incubating 2-keto-L-gulonic acid or 2-keto-D-gluconic acid, each as the free acid or as its sodium, potassium or calcium salt, and the cells of a thermoacidophilic microorganism at temperatures from about 30° C. to about 100° C., and at a pH from about 1 to about 6, in a solution, to form L-ascorbic acid or D-erythorbic acid or an appropriate salt thereof, and isolating said product from the solution.

16 Claims, No Drawings

MICROBIAL PROCESS FOR PRODUCING L-ASCORBIC ACID, D-ERYTHORBIC ACID, AND SALTS THEREOF

FIELD OF INVENTION

The present invention relates to a novel microbial process for producing L-ascorbic acid and D-erythorbic acid and salts thereof. More specifically, the present invention relates to a process for producing L-ascorbic acid or D-erythorbic acid from 2-keto-L-gulonic acid or 2-keto-D-gluconic acid, respectively, using a thermoacidophilic microorganism. The present invention also relates to a process for producing salts of L-ascorbic acid or D-erythorbic acid from salts of L-gulonic acid or 2-keto-D-gluconic acid, respectively, using a thermoacidophilic microorganism.

BACKGROUND OF THE INVENTION

L-Ascorbic acid (vitamin C) is widely used in health care as well as in preparing food and animal feed, such as, for example, fish feed, and in cosmetics. D-Erythorbic acid is mainly used as an antioxidant for food additives.

L-Ascorbic acid has been produced from D-glucose by the well-known Reichstein method (Helv. Chim. Acta 17, 311–328, 1934). In this multi-step method, L-ascorbic acid is produced chemically from the intermediate 2-keto-L-gulonic acid. The method has been used commercially for more than 60 years, during which time many chemical and technical modifications have been made to improve the efficiency of the steps that produce the intermediates D-sorbitol, L-sorbose, diacetone-L-sorbose, diacetone-2-keto-L-gulonic acid, 2-keto-L-gulonic acid, and methyl 2-keto-L-gulonate, as well as improving the efficiency of the final product, L-ascorbic acid. The conversion of D-sorbitol to L-sorbose is the sole microbial step, the others being chemical steps. The conversion of diacetone-2-keto-L-gulonic acid into L-ascorbic acid has been performed by two different procedures: 1) deprotection to give 2-keto-L-gulonic acid, followed by esterification with methanol and base-catalyzed cyclization; and 2) acid-catalyzed cyclization to L-ascorbic acid directly from the protected or deprotected 2-keto-L-gulonic acid. These conversion processes must be performed in non-aqueous or low-aqueous reaction media. Environmentally and economically, carrying out the reaction in the absence of organic solvents is preferred.

D-erythorbic acid has been produced from D-glucose via 2-keto-D-gluconic acid. 2-keto-D-gluconic acid can be produced by fermentation using a strain belonging to the genus Pseudomonas, and via methyl 2-keto-D-gluconate.

Much time and effort has been devoted to finding other methods of producing L-ascorbic acid using microorganisms. Most studies on the microbial production of L-ascorbic acid have focused on the production of the intermediate 2-keto-L-gulonic acid, particularly from L-sorbose (G. Z. Yin et al., Sheng Wu Hsueh Pao. 20, 246–251, 1980; A. Fujiwara et al., European Patent Publication No.213 591; T. Hoshino et al., U.S. Pat. No. 4,960, 695; and I. Nogami et al., European Patent Publication No. 221 707), from D-sorbitol (A. Fujiwara et al., European Patent Publication No. 213 591; T. Hoshino et al., U.S. Pat. No. 5,312,741; M. Niwa et al., W.I.P.O. Publication No. 95/23220; and S. F. Stoddart et al., WO 98/17819), or from D-glucose via 2,5-diketogluconic acid, with a single, mixed, or recombinant culture (T. Sonoyama et al., Appl. Environ. Microbiol. 43, 1064–1069, 1982; and S. Anderson et al., Science 230, 144–149, 1985). The 2-keto-L-gulonic acid can then be converted into L-ascorbic acid by chemical means, as described above.

The use of a biological process for the conversion of 2-keto-L-gulonic acid ester into L-ascorbic acid has recently been reported in Hubbs, U.S. Pat. No. 6,022,719 ("'719 patent"). This patent discloses a process for producing L-ascorbic acid by contacting 2-keto-L-gulonic acid, or an ester thereof, with a hydrolase enzyme catalyst, such as, for example, a protease, an esterase, a lipase, or an amidase. The '719 patent discloses the formation of L-ascorbic acid from an ester of 2-keto-L-gulonic acid, such as, for example, butyl 2-keto-L-gulonate, but not the formation of L-ascorbic acid from 2-keto-L-gulonic acid itself. For example, it discloses that a *Candida antartica* B lipase catalyzed reaction formed 413 to 530 mg/l of methyl 2-keto-L-gulonate, but no L-ascorbic acid, from 1% (w/v) 2-keto-L-gulonic acid in the presence of 8.6% methanol, at a pH of from 3.1 to 3.2, at 38° C. The ester synthetic activity of *Candida antartica* B lipase on 2-keto-L-gulonic acid, an α-keto-carboxylic acid, at an acidic pH, was apparently positive. However, intramolecular ester formation by this lipase was negligible.

In addition to the hydrolase reaction, ester bond synthesis reactions, such as those used for the formation of proteins (amino-esters), fatty acid esters (carboxyl-esters), and nucleotide chains (phospho-esters), are all highly functional in cells. Even in the aqueous phase, these ester bond synthesis reactions proceed unidirectionally, and are seldom inhibited by the product, particularly when compared with the reverse reaction of a hydrolase. These reaction systems require a supply of activated esters, such as, for example, activated transfer ribonucleic acid (tRNA), adenosine triphosphate (ATP), acyl coenzyme A (acyl-CoA), and the like, which are generated by energy-converting metabolism in cells. The "in vitro" reconstitution of these reactions requires a stoichiometric supply, or a regeneration system, of energy donors (e.g., ATP). Such energy donors are expensive to use in the commercial production of vitamins, as well as other chemicals, such as L-ascorbic acid and D-erythorbic acid. Thus, the utilization of intact cells is one of the more preferred commercial methods.

The chemical conversion of 2-keto-L-gulonic acid to L-ascorbic acid via 2-keto-L-gulonic acid γ-lactone is an acid-catalyzed reaction accompanied by the elimination of a water molecule. The principle step in the reaction is a carboxyl ester bond formation to form a γ-lactone ring in a 2-keto-L-gulonic acid molecule. Therefore, especially in the aqueous phase, the final state of the equilibrium reaction is determined by physico-chemical conditions. The productivity of L-ascorbic acid from 2-keto-L-gulonic acid by chemical conversion is considerable, even in the aqueous phase, but it is not sufficient for commercial application. However, performing the process in the aqueous phase, or in an aqueous phase with a low content of an organic solvent, is highly desirable due to its cost effectiveness, and for complying with environmental demands. Accordingly, the biological enhancement of the chemical conversion would be desirable for production in the aqueous phase.

Both high temperature and acidic (i.e., low) pH are desirable reaction parameters for improving the efficiency of the chemical reaction. However, in general, such physico-chemical conditions are known to be biologically incompatible with the cell survival and/or cellular activity of most microorganisms viable under mesophilic conditions. The utilization of thermophilic or acidophilic microorganisms is well known. However, there have been few examples using thermoacidophilic microorganisms which have tolerance to both heat and acid.

SUMMARY OF THE INVENTION

It has now been found that the conversion of 2-keto-L-gulonic acid, as the free acid or as its sodium potassium or calcium salt, to L-ascorbic acid, or the respective salt, in the aqueous phase, can be directly and favorably performed by thermoacidophilic microorganisms under biologically extreme conditions, such as, for example, at high temperature and low (i.e., acidic) pH. It has further been found that the conversion of 2-keto-D-gluconic acid, as the free acid or as its sodium, potassium or calcium salt, to D-erythorbic acid, or the respective salt, in the aqueous phase, can also be directly and favorably performed by thermoacidophilic microorganisms under biologically extreme conditions.

One embodiment of the present invention is a process for producing L-ascorbic acid, or a sodium, potassium or calcium salt thereof from 2-keto-L-gulonic acid, or a sodium, potassium or calcium salt of 2-keto-L-gulonic acid involving: incubating in a solution a substrate having 2-keto-L-gulonic acid as a free acid or as a sodium, potassium or calcium salt of 2-keto-L-gulonic acid, and a thermoacidophilic microorganism at about 30° C. to about 100° C. and at a pH from about 1 to about 6 to form L-ascorbic acid or a salt thereof; and isolating the L-ascorbic acid or salt thereof from the microorganism or the solution.

Another embodiment of the present invention is a process for producing D-erythorbic acid, or a sodium, potassium or calcium salt thereof from 2-keto-D-gluconic acid or a sodium, potassium or calcium salt of 2-keto-D-gluconic acid involving: incubating in a solution a substrate comprising 2-keto-D-gluconic acid as a free acid or as a sodium, potassium or calcium salt of 2-keto-D-gluconic acid, and a thermoacidophilic microorganism at about 30° C. to about 100° C. and at a pH from about 1 to about 6 to form D-erythorbic acid or a salt thereof; and isolating the D-erythorbic acid or salt thereof from the microorganism or the solution.

Another embodiment of the present invention is an isolated microorganism selected from the group consisting of Alicyclobacillus sp. NA-20 (DSM No. 13649), Alicyclobacillus sp. NA-21 (DSM No. 13650), and Alicyclobacillus sp. FJ-21 (DSM No. 13651).

A further embodiment of the present invention is a process for producing L-ascorbic acid or a salt thereof from 2-keto-L-gulonic acid or a salt thereof involving:

(a) contacting 2-keto-L-gulonic acid with a microorganism selected from the group consisting of Alicyclobacillus sp. NA-20 (DSM No. 13649), Alicyclobacillus sp. NA-21 (DSM No. 13650), and Alicyclobacillus sp. FJ-21 (DSM No. 13651) in a culture medium sufficient to support the growth of the microorganism under the following conditions:
   (i) a temperature of about 30° C. to about 100° C.; and
   (ii) a pH from about 1 to about 6; and
(b) isolating the L-ascorbic acid or a salt thereof from the microorganism or the medium.

Another embodiment of the present invention is a process for producing D-erythorbic acid, or a salt thereof from 2-keto-D-gluconic acid or a salt thereof involving:

(a) contacting 2-keto-D-gluconic acid with a microorganism selected from the group consisting of Alicyclobacillus sp. NA-20 (DSM No. 13649), Alicyclobacillus sp. NA-21 (DSM No. 13650), and Alicyclobacillus sp. FJ-21 (DSM No. 13651) in a culture medium sufficient to support the growth of the microorganism under the following conditions:
   (i) a temperature of about 30° C. to about 100° C.; and
   (ii) a pH from about 1 to about 6; and
(b) isolating the D-erythorbic acid or a salt thereof from the microorganism or the medium.

A further embodiment of the present invention is a microorganism that produces L-ascorbic acid or a salt thereof or D-erythorbic acid or a salt thereof having the following characteristics:

(a) an rDNA sequence that is at least 98.1% identical to SEQ ID NO: 1, 2 or 3 using the Genetyx-SV/R software program;
(b) a rod-shaped morphology;
(c) a width of about 0.8 $\mu$m;
(d) an inability to grow under anaerobic conditions;
(e) exhibiting catalase activity;
(f) $\overline{\omega}$-Cycohexylic acid as its major fatty acid;
(g) an ability to grow at a pH of 3.0 and a temperature of 60° C.;
(h) an inability to grow under the following conditions:

| pH  | Temperature |
|-----|-------------|
| 3.0 | 30° C.      |
| 6.5 | 60° C.      |
| 6.5 | 30° C.      |

(i) an ability to produce a (1) L-ascorbic acid or a salt thereof from 2-keto-L-gulonic acid or a salt thereof, (2) D-erythorbic acid or a salt thereof from 2-keto-D-gluconic acid or a salt thereof, or (3) both L-ascorbic acid or a salt thereof and D-erythorbic acid or a salt thereof from 2-keto-L-gulonic acid or a salt thereof and 2-keto-D-gluconic acid or a salt thereof, respectively.

DETAILED DESCRIPTION OF THE INVENTION

The process of the present invention involves incubating 2-keto-L-gulonic acid or 2-keto-D-gluconic acid, each as the free acid, or as its sodium, potassium, or calcium salt, and cells of a thermoacidophilic microorganism capable of producing and/or enhancing the production of L-ascorbic acid, or its sodium, potassium, or calcium salt, from 2-keto-L-gulonic acid, or its sodium, potassium, or calcium salt, or D-erythorbic acid, or its sodium, potassium, or calcium salt, from 2-keto-D-gluconic acid, or its sodium, potassium or calcium salt, at a high temperature (i.e. at temperatures from about 30° C. to about 100° C.) and at an acidic pH (i.e. at a pH from about 1 to about 6), in a solution as shown in Example 2, hereinafter, and isolating the L-ascorbic acid, or its sodium, potassium, or calcium salt, or D-erythorbic acid, or its sodium, potassium, or calcium salt, from the solution.

As used herein, "or its sodium, potassium or calcium salt" or an equivalent expression as applied to "2-keto-L-gulonic acid", "2-keto-D-gluconic acid", "L-ascorbic acid", or "D-erythorbic acid" will be referred to hereinafter as "or its salt". Moreover, any given concentrations of these acids or their salt forms will be expressed as being based on the free acid form even though a salt form may be present, unless clearly stated for the particular acid, or the respective salt form that is present.

As used herein, a "thermophilic microorganism" is a microorganism with optimal growth at a temperature above about 55° C. As used herein, an "acidophilic microorganism" is a microorganism with optimal growth at a pH in the acidic range, preferably below about pH 6, and no growth at a pH in the neutral range (i.e., in the pH range from about 6 to about 8). Thus, a "thermoacidophilic microorganism" is a microorganism with both of these properties, i.e., optimal growth at a temperature above about 55° C., and at a pH below about 6, and no growth in the pH range from about 6 to about 8. The term "thermoacidophilic microorganism", as used herein, also includes mutants of a thermoacidophilic microorganism, which also have the above-defined temperature and pH growth characteristics.

The term "growth" as used in the present invention means that a colony formation can be observed after 20 hours of incubation. The term "no growth" as used in the present invention means that no colonies are observed after incubation for 20 hours.

Normally, thermoacidophilic microorganisms can be prokaryotes, or can be isolated from prokaryotes, and are classified under both Archaea and Bacteria. In the Archaea domain, the genera Sulfolobus (T. D. Brock et al., Arch. Mikrobiol. 84, 54–68, 1972) and Thermoplasma (M. DeRosa et al., Phytochemistry 170, 1416–1418, 1970), are well-known thermoacidophilic microorganisms. The genera Acidanus (A. H. Segerer et al., Int. J. Syst. Bacteriol. 36, 559–564, 1986), Desulfurolobus (W. Zilling et al., Syst. Appl. Microbiol. 8, 197–209, 1986), Metallosphaera (G. Huber et al., Syst. Appl. Microbiol. 12, 38–47, 1989), Picrophilus (C. Schleper et al., J. Bacteriol. 177, 7050–7059, 1995), and Stygiolobus (A. H. Segerer et al., Int. J. Syst. Bacteriol. 41, 495–501, 1991), have also been reported as being thermoacidophilic microorganisms of the Archaea domain. In the Bacteria domain, the genera Acidimicrobium (D. A. Clark et al., Microbiology 142, 785–790, 1996), Acidothermus (F. Rainey et al., FEMS Microbiol. Lett., 108, 27–30, 1993), Sulfobacillus (R. S. Golovacheva et al., Microbiology 47, 658–665, 1978) and Alicyclobacillus (G. Darland et al. J. Gen. Microbiol. 67, 9–15, 1971; G. Deinhard et al., Syst. Appl. Microbiol. 10, 47–53, 1987) are thermoacidophilic microorganisms.

Thermoacidophilic microorganisms that can be used in the present invention include any thermoacidophilic microorganism which is capable of producing and/or enhancing the production of L-ascorbic acid, or its salt, from 2-keto-L-gulonic acid, or its salt, or the production of D-erythorbic acid, or its salt, from 2-keto-D-gluconic acid, or its salt.

The thermoacidophilic microorganisms used in the present invention can be obtained from any kind of natural source, such as, for example, soils and hot spring water, as well as from artificial sources, such as, for example, processed acidic foods and beverages (e.g., fruit juices and mixed fruit/vegetable juices).

The more extreme the conditions (ie., the higher the temperature and the lower (i.e., more acidic) the pH) under which any particular thermoacidophilic microorganism displays tolerance, the more preferably this microorganism is used in the process of the present invention. Besides tolerance to heat and acidity, thermoacidophilic microorganisms which are also tolerant to a high concentration (i.e., from about 5% to about 20% (w/v)) of 2-keto-L-gulonic acid or its salt, or of 2-keto-D-gluconic acid, or its salt, in solution, when incubated at high temperature and acidic pH, are also preferably used in the process. In addition, thermoacidophilic microorganisms with the aerobic and chemoorganotrophic characteristics described herein are preferred for the efficient (i.e., rapid) production of cells.

Preferred thermoacidophilic microorganisms are those derived from prokaryotes, including bacteria and archaea. More preferred microorganisms are thermoacidophilic bacteria. Especially preferred thermoacidophilic microorganisms are bacteria belonging to the genus Alicyclobacillus.

Among thermoacidophilic bacteria, the genus Alicyclobacillus embraces most of the strictly aerobic, spore-forming, rod-shaped and chemoorganotrophic bacteria. These microorganisms were initially assigned to the genus Bacillus. However, phylogenetic analysis based on sequence comparisons of the 16S rRNA gene has shown that the genus Alicyclobacillus belongs to a distinct line of descent within the low G+C Gram-positive lineage of Bacillus (J. D. Wisotzkey et al., Int. J. Syst. Microbiol. 42, 263–269, 1992). The three validly taxonomically described species of the genus Alicyclobacillus (A.) are: $A.$ $acidocaldarius$ (DSM $446^T$, G. Darland et al., J. Gen. Microbiol. 67, 9–15, 1971), $A.$ $acidoterrestris$ (DSM $3922^T$, G. Deinhard et al., Syst. Appl. Microbiol. 10, 47–53, 1987) and $A.$ $cycloheptanicus$ (DSM $4006^T$, G. Deinhard et al., Syst. Appl. Microbiol. 10, 68–73, 1987). Besides sequence comparisons of the 16S rRNA genes, the most distinguishable characteristic of these microorganisms is the presence of structural units of ω-cyclohexyl fatty acids (ω-cyclohexylundecanoic acid, ω-cyclohexyltridecanoic acid) or of ω-cycloheptyl fatty acids (ω-cycloheptylundecanoic acid, ω-cycloheptyltridecanoic acid) in their cellular membranes (L. Albuquerque et al., Int. J. Syst. Evol. Microbiol. 50, 451–457, 2000). Several strains with the characteristics of the genus Alicyclobacillus have been isolated so far from acidic soils within geothermal areas and from certain non-geothermal soils. In addition to soil samples, they have also been isolated from many acidic beverages as spoilage bacteria (G. Cerny et al., Z Lebens Unters Forsch 179, 224–227, 1984; K. Yamazaki et al., Biosci. Biotech. Biochem. 60, 543–545, 1996; M. Niwa et al., Japanese Patent Publication (Kokai) No. 140696/1996). Recently, in addition to the three validly named species, a wide diversity of genospecies among the genus Alicyclobacillus have been proposed. (A. Hiraishi et al., J. Gen. Appl. Microbiol. 43, 295–304, 1997; L. Albuquerque et al., Int. J. Syst. Evol. Microbiol. 50, 451–457, 2000).

Preferred thermoacidophilic microorganisms used in the present invention have the following characteristics:

1) Thermoacidophilic growth:
   Showing growth at pH 3.0 at 60° C. in 20 hours, but showing no growth at pH 3.0 at 30° C., or at pH 6.5 at 30° C., or at pH 6.5 at 60° C., in 20 hours.
2) ω-cyclohexyl fatty acids:
   Having ω-cyclohexyl fatty acid structural units in their cellular membranes according to gas chromatography-mass spectrometry (GC/MS) analysis.
3) 16S rRNA sequence similarity:
   Phylogenic analysis of 16S genes coding for rRNA sequences confirms the allocation to the genus Alicyclobacillus.

The thermoacidophilic microorganisms used in the present invention can be obtained from natural and artificial sources, as indicated above, or commercially from culture depositories. For isolating the microorganisms from natural and artificial sources, the appropriate microorganism source, such as, for example, a natural source soil or hot spring water, or an artificial source, such as, for example, processed acidic food or beverage, is preferably cultured in an aqueous medium and/or on a solid medium, supplemented with appropriate nutrients under aerobic conditions. The cultivation is preferably conducted at temperatures above about 40°

C. and at a pH below about 5, more preferably above about 50° C. and below about pH 4, and most preferably above about 55° C. and below about pH 3.5. While the cultivation period varies depending upon the pH, temperature, and nutrient medium used, a period of 12 hours to several days will generally give favorable results.

Thermoacidophilic microorganisms belonging to the genus Alicyclobacillus and which are most preferably used in the present invention are Alicyclobacillus sp. DSM No. 13652 and DSM No. 13653, which can be obtained from the Deutsche Sammlung von Mikroorganismen und Zellkulturen GmbH (DSM), Mascheroder Weg 1b, D-38124 Braunschweig, Germany, and the new strains, Alicyclobacillus sp. NA-20 and NA-21, which were isolated from a soil sample collected at Iwate Prefecture, Japan, and Alicyclobacillus sp. FJ-21, which was isolated from a commercial acidic beverage (i.e., fruit juice) purchased at Kamakura-shi, Kanagawa Prefecture, Japan.

All five of these thermoacidophilic microorganisms were deposited under the Budapest Treaty on Aug. 16, 2000 at the DSM and were allotted the following accession numbers:

Alicyclobacillus sp. DSM No. 13652
Alicyclobacillus sp. DSM No. 13653
Alicyclobacillus sp. NA-20: DSM No. 13649
Alicyclobacillus sp. NA-21: DSM No. 13650
Alicyclobacillus sp. FJ-21: DSM No. 13651

As indicated above, mutants of the above mentioned thermoacidophilic microorganisms can also be used. A mutant of a microorganism according to the present invention may be obtained by treating a wild type strain with a mutagen, such as, for example, by irradiation with ultraviolet rays, X-rays, $\gamma$-rays, or by contact with nitrous acid or other suitable mutagens. A mutant may also be obtained by isolating a clone occurring by spontaneous mutation, which may be effected using methods known by skilled artisans for such purposes. Many of these methods have been described in specialized publications, such as, for example, "Chemical Mutagens" edited by Y. Tajima, T. Yoshida and T. Kada, Kodansha Scientific Inc., Tokyo, Japan, 1973.

As used herein, a "mutant" is any microorganism that contains a non-native polynucleotide sequence or a polynucleotide sequence that has been altered from its native form (such as, for example, by rearrangement or deletion or substitution of from 1–100, preferably 20–50, more preferably less than 10 nucleotides). As noted above, such a non-native sequence may be obtained by random mutagenesis, chemical mutagenesis, UV-irradiation, and the like. Preferably, the mutation results in the increased production (compared to a non-mutant parental strain using the assay procedures set forth in the Examples) of L-ascorbic acid, D-erythorbic acid, salts of L-ascorbic acid and D-erythorbic acid, and combinations thereof. Methods for generating, screening for, and identifying such mutant cells are well known in the art.

Moreover, biologically and taxonomically homogeneous cultures of Alicyclobacillus sp. DSM No. 13652, DSM No. 13653, NA-20 (DSM No. 13649), NA-21 (DSM No. 13650), or FJ-21 (DSM No. 13651), can be used. As used herein, "biologically and taxonomically homogeneous cultures" are cultures showing the following biological and taxonomical characteristics:

growth: aerobic and thermoacidophilic
spore: forming
cell morphology: rod-shaped
major fatty acids: ω-cyclohexyl fatty acids
phylogenetical position: closest (i.e., more than 90% identity in the nucleotide sequence of 16S rRNA gene) to the strains classified in the genus Alicyclobacillus, such as, for example, Alicyclobacillus sp. DSM No. 13652, A. sp. UZ-1, A. sp. MIH-2, A. sp. KHA-31 and A. acidocaldarius DSM446$^T$, whereby the identity in the nucleotide sequence is defined using the Nucleotide Sequence Homology program (Genetyx-SV/R, version 4.0, Software Development Co., Tokyo, Japan) with default conditions (unit size to compare=1)

The above mentioned thermoacidophilic microorganisms can be used in any form, preferably as intact cells, modified cells, or immobilized cells. Methods for immobilizing cells are well known in the art (see, for example, W. M. Fogarty et al., Microbial Enzymes and Biotechnology, $2^{nd}$ Edition, Elsevier Applied Science, pp. 373–394 (1983), and Japanese Patent Publication No. 61265/1994).

Thermoacidophilic microorganisms can be screened to assess their suitability for use in the process of the present invention by the following method:

The appropriate microorganism source is cultured in an aqueous medium containing the substrate 2-keto-L-gulonic acid, or its salt, or 2-keto-D-gluconic acid, or its salt, and supplemented with appropriate nutrients under moderately aerobic conditions (i.e., under aerobic incubation without enforced aeration or vigorous agitation). The concentration of the substrate, 2-keto-L-gulonic acid, or its salt, or 2-keto-D-gluconic acid, or its salt, for carrying out the cultivation may be from about 3% (w/v) to about 20% (w/v), preferably from about 4% (w/v) to about 18% (w/v), and more preferably from about 5% (w/v) to about 16% (w/v). The incubation may be conducted at pHs from about 0.5 to about 4.0, preferably from about 1.0 to about 3.5, and more preferably from about 1.5 to about 3.0, and at temperatures from about 45° C. to about 90° C., preferably from about 50° C. to about 85° C., and more preferably from about 55° C. to about 80° C. While the incubation period varies depending upon the pH, temperature, and nutrient medium used, a period of about 12 hours to several days will generally give favorable results. After the incubation, the suitability of the screened thermoacidophilic microorganism in the process of the present invention may be assessed by its degree of productivity, (i.e., product accumulation) of L-ascorbic acid, or its salt, or D-erythorbic acid, or its salt, compared with the productivity in a "blank" incubation (i.e. without the thermoacidophilic microorganism), whereas an over 2-fold increase of productivity over the productivity in a "blank" incubation is preferred.

In the incubation described above, the presence of a high concentration of the substrate, 2-keto-L-gulonic acid, or its salt, or 2-keto-D-gluconic acid, or its salt, in addition to a high temperature and an acidic pH, may present extreme physico-chemical conditions even for a thermoacidophilic microorganism. The tolerance to 2-keto-L-gulonic acid, or its salt, or 2-keto-D-gluconic acid, or its salt, at high temperature and acidic pH is an important characteristic of the thermoacidophilic microorganisms used in the process of the present invention for maintaining cell viability.

The incubation for producing, and/or enhancing the production of, L-ascorbic acid, or its salt, from 2-keto-L-gulonic acid, or its salt, or D-erythorbic acid, or its salt, from 2-keto-D-gluconic acid, or its salt, with cells of a thermoacidophilic microorganism in the process of the present invention is effected in an aqueous phase solution. The solvent for the aqueous phase is preferably water alone (i.e., without any added other solvent(s)). If an additional solvent is used, however, a lower alkanol such as methanol is preferred.

The incubation for producing, and/or enhancing the production of, L-ascorbic acid from 2-keto-L-gulonic acid, or D-erythorbic acid from 2-keto-D-gluconic acid, each of these products or substrates being present as the free acid or the respective sodium, potassium, or calcium salt, requires nutrients, such as, for example, assimilable carbon sources, digestible or assimilable nitrogen sources, and inorganic substances, trace elements, vitamins, L-amino acids, and other growth promoting factors. As assimilable carbon sources, D-glucose, sucrose, D-glucono-δ-lactone, starch and the like can be employed. Various organic or inorganic substances may be employed as nitrogen sources, such as, for example, yeast extract, meat extract, peptone, casein, corn steep liquor, urea, amino acids, nitrates, ammonium salts, such as, for example, ammonium sulfate, and the like. As inorganic substances, magnesium sulfate, potassium phosphate, sodium chloride, potassium chloride, calcium chloride, and the like, may be employed. Furthermore, as trace elements, sulfates) hydrochlorides or phosphates of calcium, magnesium, zinc, manganese, cobalt and iron, may be employed. Preferred as inorganic salts are monopotassium phosphate, magnesium sulfate, ferrous sulfate and manganese sulfate. If necessary, conventional nutrient factors, or an antifoaming agent, such as, for example, animal oil, vegetable oil or mineral oil, can be added.

The conditions of the incubation may vary depending on the species and genetic character of the thermoacidophilic microorganism employed. The incubation is effected at what is considered to be a high temperature for an incubation (i.e., at temperatures from about 30° C. to about 100° C., preferably from about 40° C. to about 95° C., most preferably from about 55° C. to about 95° C.), at an acidic pH (i.e., at a pH from about 1.0 to about 6.0, preferably from about 1.0 to about 4.5, most preferably from about 1.5 to about 3.0), under aerobic conditions. Normally, an incubation period ranging from about 1 to about 100 hours is sufficient.

The suitable initial concentration of 2-keto-L-gulonic acid, or its salt, or of 2-keto-D-gluconic acid, or its salt, for the incubation depends on the particular thermoacidophilic microorganism used. However, a concentration of 2-keto-L-gulonic acid, or its salt, or of 2-keto-D-gluconic acid, or its salt, from about 5% (w/v) to about 20% (w/v), preferably from about 10% (w/v) to about 15% (w/v), based on the (equivalent) amount of free acid, is generally used.

The process of the present invention shows the following characteristics:

a) Specific production rate of L-ascorbic acid or its salt:
The specific production rate for L-ascorbic acid is, for example (in the presence of 8% (w/v) 2-keto-L-gulonic acid, the substrate, and 2.5 g/L L-ascorbic acid, the product, at 59° C. and pH 2.5, for 20 hours by the strain NA-21 (DSM No. 13650)) about 2.3 mg of L-ascorbic acid/mg of crude cellular protein/hour. This is based on the results given in Example 7, hereinafter.

b) Product inhibition:
The production, in the process of the present invention, is seldom inhibited by the product, L-ascorbic acid, or its salt, or D-erythorbic acid, or its salt. In addition, the process of the present invention may provide higher conversion yields than those obtained by reversible reactions in the aqueous phase.

The L-ascorbic acid, or its salt, or D-erythorbic acid, or its salt, formed in solution may be isolated, i.e., separated and/or purified, by conventional methods known in the art. The respective products may be isolated from the medium or the cells depending on the circumstances. If the product is the sodium, potassium or calcium salt of the respective acid, this salt may, if desired, be converted into the respective free acid by conventional methods known in the art. In each case, isolation of the product may be effected by methods relying upon the differences in properties between the product and impurities (including the non-converted substrate), such as, for example, solubility, adsorbability, electrochemical properties, and the distribution coefficient between two solvents. The use of an absorbent, such as, for example, an ion exchange resin, is a convenient method for isolating the product. An electro-dialysis system is another convenient method for isolating the product. If the product is insufficiently pure for its subsequent use, it may be purified by conventional methods, such as, for example, recrystallization and chromatography.

L-Ascorbic acid can be produced from L-sorbose or D-sorbitol by using a combination of organisms, one organism having the ability to convert 2-keto-L-gulonic acid to L-ascorbic acid, or 2-keto-D-gluconic acid to D-erythorbic acid, the other organism having L-sorbose/L-sorbosone dehydrogenase and D-sorbitol dehydrogenase, and the ability to convert D-sorbitol and/or L-sorbose to 2-keto L-gulonic acid (see A. Fujiwara et al., EP 213 591; T. Hoshino et al., U.S. Pat. No. 4,960,695; T. Hoshino et al, U.S. Pat. No. 5,312,741), such as, for example, *Gluconobacter oxydans* DSM 4025 in a one-step conversion with one vessel, or a two-step conversion with two vessels.

D-Erythorbic acid can be produced from D-glucose or D-gluconic acid by using a combination of organisms, one having the ability to convert 2-keto-L-gulonic acid to L-ascorbic acid, or 2-keto-D-gluconic acid to D-erythorbic acid, the other having D-glucose dehydrogenase (Ameyama et al., Agric Biol. Chem. 45:851–861, 1981) and/or D-gluconate dehydrogenase (Shinagawa et al., Agric Biol. Chem. 48: 1517–1522, 1984), such as, for example, *Gluconobacter dioxyacetonicus* IFO 3271, which can convert D-glucose and/or D-gluconic acid to 2-keto-D-gluconic acid in a one-step conversion with one vessel, or a two step-conversion with two vessels.

The following Examples are provided to further illustrate the process of the present invention. These examples are illustrative only and are not intended to limit the scope of the invention in any way.

EXAMPLES

Example 1

Screening of Thermoacidophilic Microorganisms

A) Isolation from soil samples

Soil samples collected at an acidic hot spring area at Iwate Prefecture in Japan were used for the screening. Thermoacidophilic microorganisms were recovered from the soil samples in 0.9% (w/v) NaCl solution, and isolated by spreading the solution on 573c (pH 3.5) agar plate medium containing 0.1% (w/v) of D-glucose, 0.13% (w/v) of $(NH_4)_2SO_4$, 0.1% (w/v) of yeast extract, 0.15% (w/v) of $KH_2PO_4$, 0.025% (w/v) of $MgSO_4 \cdot 7H_2O$, 0.007% (w/v) of $CaCl_2 \cdot 2H_2O$ and 2% (w/v) of agar (the pH was adjusted by 6N $H_2SO_4$; D-glucose and agar were sterilized separately). After incubation at 60° C. for 20 hours, single colonies grown at pH 3.5 and 60° C. were randomly collected and purified by transferring them three times onto the same agar plate medium, under the same conditions. The resulting isolated microorganisms were numbered and designated as belonging to the "NA" series. For example, one such isolated microorganism was designated as NA-20, another as NA-21.

B) Isolation from acidic beverages

Various commercial acidic beverages, i.e. fruit juice products and mixed fruit/vegetable juice products, were subjected to experiments for isolating thermoacidophilic microorganisms therefrom. In each case, 1 ml of the commercial product was centrifuged and the resulting pellet was washed with 1 ml of sterilized distilled water to obtain a washed pellet. The pellet was suspended in 0.1 ml of sterilized distilled water, and the suspension was spread on an agar plate of medium 573c. The plate was then incubated at 60° C. for 1 to 3 days to observe single colonies. The colonies were purified by transferring them three times onto the same agar plate medium, under the same conditions. The resulting isolated microorganisms were numbered and designated as belonging to the "FJ" series. For example, one such isolated microorganism was designated as FJ-21.

Example 2
Screening of NA- and FJ-Series Isolated Microorganisms for Production of L-ascorbic Acid from 2-keto-L-gulonic Acid Screening for the production of L-ascorbic acid from 2-keto-L-gulonic acid was performed using the following living cell reaction system: Compositions of LM101 type media, mineral mixture [MM], vitamin mixture [VM], and amino acid mixture [AM], are listed in Table 1 below.

TABLE 1

Table 1a: Media (salt base)

| | LM101c [g/L] | LM101d [g/L] |
|---|---|---|
| D-glucose | variable | variable |
| $(NH_4)_2SO_4$ | 4 | 1.3 |
| $KH_2PO_4$ | 1.5 | 1.5 |
| $MgSO_4 \cdot 7H_2O$ | 0.25 | 0.25 |
| NaCl | 0.1 | 0.1 |
| KCl | 0.1 | 0.1 |
| $CaCl_2 \cdot 2H_2O$ | 0.07 | 0.07 |
| pH | 2.5[a] | 2.5[b] |

Table 1b

| Mineral Mixture [× 1000 conc.] | [mg/L] |
|---|---|
| $CuSO_4 \cdot 5H_2O$ | 620 |
| $FeSO_4 \cdot 5H_2O$ | 600 |
| $MnSO_4 \cdot 5H_2O$ | 600 |
| $ZnSO_4 \cdot 5H_2O$ | 600 |
| $CoCl_2 \cdot 5H_2O$ | 790 |
| $Na_2MoO_4 \cdot 5H_2O$ | 700 |

Table 1c

| Vitamin Mixture [× 100 conc.] | [mg/L] |
|---|---|
| Biotin | 100 |
| Ca(+)-Pantothenate | 100 |
| Folic acid | 100 |
| Inositol | 200 |
| Pyridoxal phosphate · $H_2O$ | 100 |
| Riboflavin | 10 |
| Thiamine · HCl | 100 |
| Nicotinamide | 100 |

Table 1d

| L-Amino Acid Mixture [× 5 conc.] | [mg/L] |
|---|---|
| Arginine · HCl | 630 |
| Cystine | 120 |
| Glutamine | 1460 |
| Histidine · HCl · $H_2O$ | 210 |
| Isoleucine | 260 |
| Leucine | 260 |
| Lysine · HCl | 360 |
| Methionine | 76 |

TABLE 1-continued

| Phenylalanine | 165 |
|---|---|
| Threonine | 240 |
| Tryptophan | 50 |
| Tyrosine | 180 |
| Valine | 230 |

[a]after the addition of sodium 2-keto-L-gulonate monohydrate, pH is adjusted by 6N $H_2SO_4$
[b]after the addition of 2-keto-L-gulonic acid, pH is adjusted by 6N KOH The thermoacidophilic microorganisms of the NA and FJ series, isolated as described in Example 1, were grown on 573c agar plate medium (pH 3.5, 60° C., 15 hours) and inoculated into medium LM101c-plus ("plus" means supplementation with MM (×1 conc.), VM (×0.1 conc.) and AM (×0.01 conc.)) containing 0.25% (w/v) of D-glucose. After aerobic cultivation in test tubes (60° C., 8 hours), the resulting cells were collected by centrifugation and used as seeding cells after suspending in LM101c salt base (at an of optical density of about 25, at 660 nm [OD660]). The cells were inoculated at a final OD660 of 0.2 into 0.8 ml of LM101c-plus medium (pH 2.5) containing 6% (w/v) of sodium 2-keto-L-gulonate monohydrate and 0.2% (w/v) of D-glucose. The resulting cell reaction mixture was incubated at 59° C. under moderately aerobic conditions; a test tube (2.0 ml micro test tube, Eppendorf, Germany) with a pin hole (0.65 mm) at the top was used, with rotary shaking (120 rpm with 45 mm radius). L-Ascorbic acid production was determined by HPLC analysis: YMC-Pack Polyamine II column (ID. 4.6×150 mm; YMC Co., Japan) at 264 nm with the mobile-phase solvent containing 70% (v/v) of acetonitrile and 15 mM of ammonium dihydrogen phosphate at a flow rate of 1.5 ml/min. The amount of water lost by evaporation was estimated as the weight decrease during the incubation, and a compensating amount of water was added to retain the original volume. After 23 hours of cultivation, the L-ascorbic acid production of each strain was compared with two control values: "aerobic blank" is the L-ascorbic acid production obtained with the same medium and conditions, but without cell inoculation, and "anaerobic control" is the L-ascorbic acid production obtained with the same medium, but without cell inoculation, in a closed micro test tube with argon gas. As a result of the screening, strains NA-20, NA-21, and FJ-21 were selected as potent L-ascorbic acid producers; they produced 1.07, 1.19 and 1.23 g/L of L-ascorbic acid, respectively. The amounts of L-ascorbic acid in the aerobic blank and anaerobic control were about 0.10 and 0.30 g/L, respectively.

The living-cell reaction with 2-keto-D-gluconic acid (hemicalcium salt containing 1.5 mol/mol $H_2O$, SIGMA Chemical Co., St. Louis, Mo., USA) was performed under the same conditions as described above, except using 1.2% (w/v) of 2-keto-D-gluconic acid instead of 6% (w/v) of sodium 2-keto-L-gulonate monohydrate, as the substrate. The production of D-erythorbic acid was determined by the same HPLC analysis method. The strain NA-21 produced 0.051 g/L of D-erythorbic acid after 23 hours incubation. The amounts of D-erythorbic acid in the aerobic blank and anaerobic control were not detectable (less than 0.001 g/L).

Example 3
Taxonomy of the Isolated Microorganisms

The three isolated microorganisms, NA-20, NA-21 and FJ-21, were aerobic, spore-forming and rod-shaped bacteria. Phenotypic characteristics of the isolates are summarized in the following Table 2.

TABLE 2

| | NA-20 | NA-21 | FJ-21 |
|---|---|---|---|
| Shape | rod | rod | rod |
| Size | | | |
| (width, μm) | 0.8 | 0.8 | 0.8 |
| (length, μm) | 2–3 | 3–5 | 2–3 |
| Gram Stain | variable | variable | negative |
| Motility | + | + | – |
| Anaerobic Growth | – | – | – |
| Oxidase Test | – | – | – |
| Catalase Test | + | + | + |
| Major Fatty Acid | ω-Cyclohexylic acids (C17 and 19) | ω-Cyclohexylic acids (C17 and 19) | ω-Cyclohexylic acids (C17 and 19) |
| Growth at[a] | | | |
| pH / Temp. (° C.) | | | |
| 3.0 / 60 | + | + | + |
| 3.0 / 30 | – | – | – |
| 6.5 / 60 | – | – | – |
| 6.5 / 30 | – | – | – |

[a] growth on 573c agar plate for 20 hours

The microorganisms showed growth at pH 3.0/60° C. in 20 hours, but not at pH 3.0/30° C., pH 6.5/30° C., and pH 6.5/60° C. in 20 hours. Therefore, they were characterized as thermoacidophilic Bacillus group bacteria. GC/MS analysis on fatty acids indicated that the major components of the three isolated microorganisms were identical with those of Alicyclobacillus acidocaldarius DSM 466[T] investigated as the control, suggesting that ω-cyclohexyl fatty acids were the major components of the isolated microorganisms as well as of Alicyclobacillus acidocaldarius DSM 466[T]. 16S rRNA gene sequences of the isolated microorganisms were determined with a 16S rRNA gene kit (PE Applied Biosystems, USA; SEQ ID NOs: 1, 2, and 3 for the strain NA-20, NA-21 and FJ-21, respectively) and were subjected to the BLAST search program (J. Mol. Biol. 215 403–410, 1990; Nucleic Acids Res. 25 3389–3402, 1997). Sequence similarity analysis using the Nucleotide Sequence Homology program (Genetyx-SV/R, version 4.0, Software Development Co., Tokyo, Japan) with default conditions (unit size to compare=1) indicated that the isolated microorganisms could belong phylogenetically to the genus Alicyclobacillus. The following Table 3 shows the levels of binary sequence identity (%) in 16S rRNA gene sequences between the isolated microorganisms and reference strains, including the three type strains.

TABLE 3

Identity (%) in 16S rRNA gene

| | | Accession No. | NA-20 | NA-21 | FJ-21 |
|---|---|---|---|---|---|
| A. acidocaldarius | DSM 446[T] | X60742 | 96.9 | 97.0 | 98.3 |
| A. acidoterrestris | DSM 3922[T] | AJ133631 | 94.0 | 94.1 | 94.5 |
| A. cycloheptanicus | DSM 4006[T] | X51928 | 92.6 | 92.6 | 92.9 |
| A. sp. | UZ-1 | AB004579 | 99.5 | 99.6 | 97.8 |
| A. sp. | MIH-2 | AB004580 | 99.5 | 99.6 | 97.8 |
| A. sp. | KHA-31 | AB004581 | 99.2 | 99.3 | 97.6 |
| A. sp. | DSM 13652 | AJ133634 | 99.0 | 99.1 | 97.6 |
| A. sp. | NA-20 | | 100.0 | 99.7 | 98.1 |
| A. sp. | NA-21 | | 99.7 | 100.0 | 98.1 |
| A. sp. | FJ-21 | | 98.1 | 98.1 | 100.0 |

The 16S rDNA sequences of NA-20 and NA-21 were most similar to each other (99.7%), and to the sequences of Alicyclobacillus sp. UZ-1, MIH-2, KHA-31 (J. Gen. Appl. Microbiol., 43, 295–304, 1997) and A. sp. DSM No. 13652 (99.0 to 99.6%). The sequence of FJ-21 was most similar to those of A. acidocaldarius DSM 446[T], NA-20, and NA-21 (98.1 to 98.3%). From these results, the three isolated microorganisms were classified into the genus Alicyclobacillus and named as Alicyclobacillus sp. NA-20, NA-21, and FJ-21, respectively.

Under the same screening conditions as described in Example 2, Alicyclobacillus sp. DSM No. 13652 and DSM No. 13653 produced 0.91 and 0.95 g/L of L-ascorbic acid from sodium 2-keto-L-gulonate monohydrate, respectively.

Example 4
Effects of Carbon/Energy Source and Aeration

In the L-ascorbic acid production process described in Example 2, a medium containing 0.2% (w/v) of D-glucose in addition to 6% (w/v) of sodium 2-keto-L-gulonate monohydrate was used to maintain cell living. For the production process using Alicyclobacillus sp. NA-21, the addition of D-glucono-δ-lactone (0.1% (w/v)), sucrose (0.1% (w/v)), or soluble starch (1% (w/v)), instead of D-glucose resulted in almost the same production of L-ascorbic acid. The absence of a carbon/energy source resulted in no additional production over the aerobic blank (see Table 4).

TABLE 4

| Carbon | [% (w/v)] | Cell | L-Ascorbic Acid [g/L][a] |
|---|---|---|---|
| Sucrose | 0.1 | + | 0.69 |
| Soluble Starch | 1.0 | + | 0.65 |
| D-Glucono-δ-lactone | 0.1 | + | 0.76 |
| D-Glucose | 0.1 | + | 0.80 |
| D-Glucose | 0.025 | + | 0.66 |
| No Carbon | – | + | 0.10 |
| Aerobic Blank | – | – | 0.09 |

[a] 13 hour production from 6% (w/v) of sodium 2-keto-L-gulonate-monohydrate

In the L-ascorbic acid production process described in Example 2, production was carried out under moderately aerobic conditions. Using Alicyclobacillus sp. NA-21, the results of carrying out the process under aerobic and anaerobic conditions were compared. The same reaction mixture in a completely closed micro test tube was used for the system under anaerobic conditions after gasification with argon gas. The aerobic conditions contributed to nearly linear production until 38 hours, but anaerobic conditions did not allow production even after 15 hours (see Table 5).

TABLE 5

| | Reaction Time [h] | | | |
|---|---|---|---|---|
| | 0 | 15 | 23 | 38 |
| L-Ascorbic acid production (g/L) under aerobic condition | | | | |
| +Cell | 0.00 | 0.80 | 1.29 | 2.10 |
| −Cell | 0.00 | 0.12 | 0.13 | 0.17 |
| L-Ascorbic acid production (g/L) under anaerobic condition | | | | |
| +Cell | 0.00 | 0.79 | 0.87 | 1.05 |
| −Cell | 0.00 | 0.25 | 0.36 | 0.59 |

Example 5

L-Ascorbic Acid Production Using, the Strain NA-21 or Its Derivatives

L-Ascorbic acid production from 6% (w/v) of sodium 2-keto-L-gulonate monohydrate was examined by using Alicyclobacillus sp. NA-21. Preparation of seeding cells was carried out by the same method as described in Example 2. The cells were inoculated at a final OD660 of 0.25 into 0.8 ml of LM101c-plus medium (pH 2.5) containing 6% (w/v) of sodium 2-keto-L-gulonate monohydrate and 0.1% (w/v) of D-glucose. The resulting cell reaction mixture was incubated at 59° C. under moderately aerobic conditions; a test tube with a pin hole (0.65 mm) at the top was used with rotary shaking (120 rpm with 45 mm radius). L-Ascorbic acid production by Alicyclobacillus sp. NA-21 continued linearly, until 38 hours, to reach 2.23 g/L of L-ascorbic acid. Productivity was more effective than that of the aerobic blank and of the anaerobic control (see Table 6).

TABLE 6

| | Reaction Time [h] | | | |
|---|---|---|---|---|
| | 0 | 15 | 23 | 38 |
| OD 660 | | | | |
| +Cell | 0.25 | 0.22 | 0.20 | 0.15 |
| −Cell | | | | |
| Aerobic Blank | 0.00 | 0.00 | 0.00 | 0.00 |
| Anaerobic Control | 0.00 | 0.00 | 0.00 | 0.00 |
| pH | | | | |
| +Cell | 2.46 | 2.46 | 2.45 | n.d. |
| −Cell | | | | |
| Aerobic Blank | 2.46 | 2.44 | 2.43 | n.d. |
| Anaerobic Control | 2.46 | 2.44 | 2.44 | n.d. |
| L-Ascorbic Acid Production [g/L] | | | | |
| +Cell | 0.00 | 0.76 | 1.25 | 2.23 |

TABLE 6-continued

| | Reaction Time [h] | | | |
|---|---|---|---|---|
| | 0 | 15 | 23 | 38 |
| −Cell | | | | |
| Aerobic Blank | 0.00 | 0.12 | 0.13 | 0.17 |
| Anaerobic Control | 0.00 | 0.25 | 0.36 | 0.59 | n.d.: not determined

Two derivatives of the original strain, Alicyclobacillus sp. NA-21, MA-10, and MB-6 were sequentially obtained by conventional mutagenesis followed by the selection steps described below. From the original strain, MA-10 was selected as a strain having tolerance against a higher 2-keto-L-gulonic acid concentration (about a 1% (w/v) improvement from 10% (w/v), at 60° C. and pH 2.5) after ultraviolet irradiation. Subsequently, from MA-10, MB-6 was selected as a strain having tolerance against a higher temperature (about a 2° C. improvement from 60° C., at 11% (w/v) of 2-keto-L-gulonic acid and pH 2.5) after treatment with N-methyl-N'-nitro-N-nitrosoguanidine. L-Ascorbic acid productivities were compared among the original strain, MA-10 and MB-6 by the same living-cell reaction described above at 62° C. and pH 2.5, using 11% (w/v) of 2-keto-L-gulonic acid and a medium containing ×0.5 conc. of LM101d salt base, 0.25%(w/v) of D-glucose, ×0.1 conc. of MM, ×0.05 conc. of VM and ×0.005 conc. of AM. The original strain, MA-10, and MB-6 produced 2.02, 2.22, and 2.80 g/L of L-ascorbic acid at 23 hours, respectively. The aerobic blank and the anaerobic control produced 1.63 and 1.94 g/L of L-ascorbic acid, respectively.

Example 6

L-Ascorbic Acid Production from 8% (w/v) 2-Keto-L-Gulonic Acid with Feeding of Cells and the Addition of D-glucose L-Ascorbic acid production from 8% (w/v) 2-keto-L-gulonic acid with feeding of cells and with the addition of D-glucose, was examined by using Alicyclobacillus sp. NA-21. Preparation of seeding cells was carried out by the same method as described in Example 2. The cells were inoculated at a final OD660 of 0.25 into 0.8 ml of LM101d-plus medium (pH 2.5) containing 8% (w/v) of 2-keto-gulonic acid and 0.15% (w/v) of D-glucose. The resulting cell reaction mixture was incubated at 59° C. under moderately aerobic conditions; a test tube with a pin hole (0.65 mm) at the top was used with rotary shaking (120 rpm with 45 mm radius). Seeding cells and D-glucose were supplied at 24 hours (0.25 of OD660 and 0.15% (w/v) at final concentration, respectively) as a spot feeding. L-Ascorbic acid production by Alicyclobacillus sp. NA-21 continued linearly until 47 hours to reach 3.70 g/L of L-ascorbic acid (see Table 7).

TABLE 7

| | L-Ascorbic Acid Production (g/L) | | | | | | | |
|---|---|---|---|---|---|---|---|---|
| Reaction Time (h) | 0 | 15 | 23 | 39 | 47 | 71 | 87 | 95 |
| + Cell | 0.00 | 1.13 | 1.97 | 2.99 | 3.70 | n.d. | n.d. | n.d. |
| − Cell | | | | | | | | |
| Aerobic Blank | 0.00 | 0.23 | 0.32 | 0.35 | 0.36 | 0.39 | 0.32 | 0.28 |
| Anaerobic Control | 0.00 | 0.49 | 0.74 | 1.20 | 1.52 | 2.26 | 2.57 | 2.44 | n.d.: not determined

On the other hand, the productivity of the anaerobic control reached a maximum at about 2.5 g/L of L-ascorbic acid, after about 80 hours.

Example 7
L-Ascorbic Acid Production from 8% (w/v) 2-Keto-L-Gulonic Acid in the Presence of L-Ascorbic Acid L-Ascorbic acid production from 8% (w/v) 2-keto-L-gulonic acid in the presence of 0–4.5 g/L of L-ascorbic acid was examined by using Alicyclobacillus sp. NA-21. Preparation of seeding cells was carried out by the same method as described in Example 2. The cells were inoculated at a final OD660 of 0.25 into 0.8 ml of LM101d-plus medium (pH 2.5) containing ×0.1 conc. of MM (instead of ×1 conc. of MM) and 8% (w/v) of 2-keto-gulonic acid and 0.20% (w/v) of D-glucose. The resulting cell reaction mixture was incubated at 59° C. under moderately aerobic conditions; a test tube with a pin hole (0.65 mm) at the top was used with rotary shaking (120 rpm with 45 mm radius) for 20 hours. To the above medium, 0.0, 1.1, 2.3, or 4.5 g/L of L-ascorbic acid (product) was added at the 0 hour time-point (before the initiation of production). The productivity of Alicyclobacillus sp. NA-21 was nearly the same in the absence and presence of the product. On the other hand, productivity of the anaerobic control was gradually repressed by the presence of a higher concentration of the product (see Table 8).

TABLE 8

From 0.0 g/L of Initial L-Ascorbic Acid

| | L-Ascorbic Acid [g/L] Reaction Time [h] | | Net Production* 20 h minus 0 h |
|---|---|---|---|
| | 0 | 20 | [g/L] |
| +Cell −Cell | 0 | 1.81 | 1.81 |
| Aerobic Blank | 0 | 0.44 | 0.44 |
| Anaerobic Control | 0 | 0.83 | 0.83 |

TABLE 8-continued

From 1.3 g/L of Initial L-Ascorbic Acid

| | L-Ascorbic Acid [g/L] Reaction Time [h] | | Net Production 20 h minus 0 h |
|---|---|---|---|
| | 0 | 20 | [g/L] |
| +Cell −Cell | 1.32 | 3.16 | 1.84 |
| Aerobic Blank | 1.32 | 0.80 | −0.52 |
| Anaerobic Control | 1.32 | 1.75 | 0.43 |

From 2.5 g/L of Initial L-Ascorbic Acid

| | L-Ascorbic Acid [g/L] Reaction Time [h] | | Net Production 20 h minus 0 h |
|---|---|---|---|
| | 0 | 20 | [g/L] |
| +Cell −Cell | 2.48 | 4.33 | 1.85 |
| Aerobic Blank | 2.48 | 1.55 | −0.93 |
| Anaerobic Control | 2.48 | 2.7 | 0.22 |

From 4.6 g/L of Initial L-Ascorbic Acid

| | L-Ascorbic Acid [g/L] Reaction Time [h] | | Net Production 20 h minus 0 h |
|---|---|---|---|
| | 0 | 20 | [g/L] |
| +Cell −Cell | 4.55 | 6.64 | 2.09 |
| Aerobic Blank | 4.55 | 3.02 | −1.53 |
| Anaerobic Control | 4.55 | 4.21 | −0.34 |

*Net Production means amount of L-ascorbic acid accumulated at 20 h minus that added at 0 h.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing L-ascorbic acid, or a sodium, potassium or calcium salt thereof from 2-keto-L-gulonic acid, or a sodium, potassium or calcium salt of 2-keto-L-gulonic acid comprising:
   a. incubating in a solution a substrate comprising 2-keto-L-gulonic acid as a free acid or a sodium, potassium or calcium salt of 2-keto-L-gulonic acid, and a thermoacidophilic microorganism at about 30° C. to about 100° C. and at a pH from about 1 to about 6 to form L-ascorbic acid or a salt thereof; and
   b. isolating the L-ascorbic acid or salt thereof from the microorganism or the solution.

2. A process according to claim 1 wherein the thermoacidophilic microorganism is a prokaryote.

3. A process according to claim 2 wherein the prokaryote is a bacteria.

4. A process according to claim 3 wherein the bacteria belongs to the genus Alicyclobacillus.

5. A process according to claim 4 wherein the bacteria is an Alicyclobacillus sp. strain selected from the group consisting of DSM No. 13652, DSM No. 13653, NA-20 (DSM No. 13649), NA-21 (DSM No. 13650), FJ-21 (DSM No. 13651), and mutants thereof.

6. A process according to claim 4 wherein the bacteria is a biologically and taxonomically homogeneous culture having the identifying characteristics of an Alicyclobacillus sp. strain selected from the group consisting of DSM No. 13652, DSM No. 13653, NA-20 (DSM No. 13649), NA-21 (DSM No. 13650), and FJ-21 (DSM No. 13651).

7. A process according claim 1 wherein the solution contains water as the solvent.

8. A process according to claim 1 wherein the incubation is carried out under aerobic conditions.

9. A process according to claim 1 wherein the incubation is carried out under aerobic conditions in the presence of nutrients.

10. A process according to claim 1 wherein the concentration of the substrate in the solution is from about 5% (w/v) to about 20% (w/v), based on the amount of free acid.

11. A process according to claim 10 wherein the concentration of the substrate in the solution is from about 10% (w/v) to about 15% (w/v), based on the amount of free acid.

12. A process according to claim 1 wherein the incubation is carried out at about 40° C. to about 95° C.

13. A process according to claim 12 wherein the incubation is carried out at about 55° C. to about 95° C.

14. A process according to claim 1 wherein the incubation is carried out at a pH from about 1.0 to about 4.5.

15. A process according to claim 14 wherein the incubation is camed out at a pH from about 1.5 to about 3.0.

16. A process for producing L-ascorbic acid or a salt thereof from 2-keto-L-gulonic acid or a salt thereof comprising:
   a. contacting 2-keto-L-gulonic acid with a microorganism selected from the group consisting of Alicyclobacillus sp. NA-20 (DSM No. 13649), Alicyclobacillus sp. NA-21 (DSM No. 13650), and Alicyclobacillus sp. FJ-21 (DSM No. 13651) in a culture medium sufficient to support the growth of the microorganism under the following conditions:
   a temperature of about 30° C. to about 100° C.; and
   ii. a pH from about 1 to about 6; and
   b. isolating the L-ascorbic acid or a salt thereof from the microorganism or the medium.

* * * * *

SEQUENCE LISTING

```
<160> NUMBER OF SEQ ID NOS: 3

<210> SEQ ID NO 1
<211> LENGTH: 1529
<212> TYPE: DNA
<213> ORGANISM: Alicyclobacillus sp.
<220> FEATURE:
<221> NAME/KEY: rRNA
<222> LOCATION: (1)..(1529)
<223> OTHER INFORMATION: NA-20 partial 16SrRNA gene sequence
<220> FEATURE:
<221> NAME/KEY: misc_feature
<222> LOCATION: (1)..(1529)
<223> OTHER INFORMATION: n can be a or t or g or c

<400> SEQUENCE: 1
agagtttgat cctggctcag gacgaacgct ggcggcgtgc ctaatacatg caagtcgagc      60
gggtctcttc ggaggccagc ggcggacggg tgaggaacac gtgggtaatc tgcctttcag    120
gccggaataa cgcccggaaa cgggcgctaa tgccggatac gcccgcgagg aggcatcttc    180
```

```
ttgcggggga aggcccaatt gggccgctga gagaggagcc cgcggcgcat tagctngttg      240
gcggggtaac ggcccaccaa ggcgacgatg cgtagccgac ctgagagggt gaccggccac      300
actgggactg agacacggcc cagactccta cgggaggcag cagtagggaa tcttccgcaa      360
tgggcgcaag cctgacggag caacgccgcg tgagcgaaga aggccttcgg gttgtaaagc      420
tctgttgctc ggggagagcg gcatggggga tggaaagccc catgcgagac ggtaccgagt      480
gaggaagccc cggctaacta cgtgccagca gccgcggtaa aacgtagggg cgagcgttg       540 tccggaatca ctgggcgtaa aggtgcgta  ggcggtcgag caagtctgga gtgaaagtcc      600
atggctcaac catgggatgg ctttggaaac tgcttgactt gagtgctgga gaggcaaggg      660
gaattccacg tgtagcggtg aaatgcgtag agatgtggag gaataccagt ggcgaaggcg      720
ccttgctgga cagtgactga cgctgaggca cgaaagcgtg gggagcaaac aggattagat      780
accctggtag tccacgccgt aaacgatgag tgctaggtgt tggggggaca cccccagtg      840 ccgaaggaaa cccaataagc actccgcctg gggagtacgg tcgcaagact gaaactcaaa      900
ggaattgacg ggggcccgca caagcagtgg agcatgtggt ttaattcgaa gcaacgcgaa      960
gaaccttacc agggcttgac atccctctga cacnctcaga gatgagggt cccttcgggg       1020 cagaggagac aggtggtgca tggttgtcgt cagctcgtgt cgtgagatgt tgggttcagt      1080
cccgcaacga gcgcaaccct tgacctgtgt taccagcgcg ttgaggcggg gactcacagg      1140
tgactgccgg cgtaagtcgg aggaaggcgg ggatgacgtc aaatcatcat gcccctgatg      1200
tcctgggcta cacacgtgct acaatgggcg gaacaaaggg aggcgaagcc gcgaggcgga      1260
gcgaaaccca aaaagccgct cgtagttcgg attgcaggct gcaactcgcc tgcatgaagc      1320
cggaattgct agtaatcgcg gatcagcatg ccgcggtgaa tacgttcccg ggccttgtac      1380
acaccgcccg tcacaccacg agagtcggca cacccgaag tcggtgaggt aaccccctnng      1440 gggagccagc cgccgaaggt ggggtcgatg attggggtga agtcgtaaca aggtagccgt      1500
accggaaggt gcggctggat cacctcctt                                        1529
```

<210> SEQ ID NO 2
<211> LENGTH: 1529
<212> TYPE: DNA
<213> ORGANISM: Alicyclobacillus sp.
<220> FEATURE:
<221> NAME/KEY: rRNA
<222> LOCATION: (1)..(1529)
<223> OTHER INFORMATION: NA-21 Partial 16SrRNA gene
<220> FEATURE:
<221> NAME/KEY: misc_feature
<222> LOCATION: (1)..(1529)
<223> OTHER INFORMATION: n can be a or t or g or c

<400> SEQUENCE: 2

```
agagtttgat cctggctcag gacgaacgct ggcggcgtgc ctaatacatg caagtcgagc       60
gggtctcttc ggaggccagc ggcggacggg tgaggaacac gtgggtaatc tgcctttcag      120
gccggaataa cgcccggaaa cgggcgctaa tgccggatac gcccgcgagg aggcatcttc      180
ttgcggggga aggcccaatt gggccactga gagaggagcc cgcggcgcat tagctngttg      240
gcggggtaac ggcccaccaa ggcgacgatg cgtagccgac ctgagagggt gaccggccac      300
actgggactg agacacggcc cagactccta cgggaggcag cagtagggaa tcttccgcaa      360
tgggcgcaag cctgacggag caacgccgcg tgagcgaaga aggccttcgg gttgtaaagc      420
tctgttgctc ggggagagcg gcatggggga tggaaagccc catgcgagac ggtaccgagt      480
```

| | |
|---|---|
| gaggaagccc cggctaacta cgtgccagca gccgcggtaa aacgtagggg gcgagcgttg | 540 |
| tccggaatca ctgggcgtaa agggtgcgta ggcggtcgag caagtctgga gtgaaagtcc | 600 |
| atggctcaac catgggatgg cttttggaaac tgcttgactt gagtgctgga gaggcaaggg | 660 |
| gaattccacg tgtagcggtg aaatgcgtag agatgtggag gaataccagt ggcgaaggcg | 720 |
| ccttgctgga cagtgactga cgctgaggca cgaaagcgtg gggagcaaac aggattagat | 780 |
| accctggtag tccacgccgt aaacgatgag tgctaggtgt tggggggaca caccccagtg | 840 |
| ccgaaggaaa cccataagc actccgcctg gggagtacgg tcgcaagact gaaactcaaa | 900 |
| ggaattgacg ggggcccgca caagcagtgg agcatgtggt ttaattcgaa gcaacgcgaa | 960 |
| gaaccttacc agggcttgac atccctctga caccctcaga gatgagggt cccttcgggg | 1020 |
| cagaggagac aggtggtgca tggttgtcgt cagctcgtgt cgtgagatgt tgggttcagt | 1080 |
| cccgcaacga gcgcaaccct tgacctgtgt taccagcgcg ttgaggcggg gactcacagg | 1140 |
| tgactgccgg cgtaagtcgg aggaaggcgg ggatgacgtc aaatcatcat gcccctgatg | 1200 |
| tcctgggcta cacacgtgct acaatgggcg gaacaaaggg aggcgaagcc gcgaggcgga | 1260 |
| gcgaaaccca aaaagccgct cgtagttcgg attgcaggct gcaactcgcc tgcatgaagc | 1320 |
| cggaattgct agtaatcgcg gatcagcatg ccgcggtgaa tacgttcccg ggccttgtac | 1380 |
| acaccgcccg tcacaccacg agagtcggca cacccgaag tcggtgaggt aacccccttag | 1440 |
| gggagccagc cgccgaaggt ggggtcgatg attggggtga agtcgtaaca aggtagccgt | 1500 |
| accggaaggt gcggctggat cacctcctt | 1529 |

<210> SEQ ID NO 3
<211> LENGTH: 1495
<212> TYPE: DNA
<213> ORGANISM: Alicyclobacillus sp.
<220> FEATURE:
<221> NAME/KEY: rRNA
<222> LOCATION: (1)..(1495)
<223> OTHER INFORMATION: FJ-21 Partial 16SrRNA gene sequence
<220> FEATURE:
<221> NAME/KEY: misc_feature
<222> LOCATION: (1)..(1495)
<223> OTHER INFORMATION: n can be a or t or g or c

<400> SEQUENCE: 3

| | |
|---|---|
| aggacgaacg ctggcggcgt gcctaataca tgcaagtcga gcggacctct tctgaggtca | 60 |
| gcggcggacg ggtgaggaac acgtgggtaa tctgcctttc agaccggaat aacgcccgga | 120 |
| aacgggcgct aatgccggat acgcccgcga ggaggcatct tcttgcgggg aaaggcccga | 180 |
| ttgggccgct gagagaggag cccgcggcgc attagctngt tggcggggta acggcccacc | 240 |
| aaggcgacga tgcgtagccg acctgagagg gtgaccggcc acactgggac tgagacacgg | 300 |
| cccagactcc tacgggaggc agcagtaggg aatcttccgc aatgggcgca agcctgacgg | 360 |
| agcaacgccg cgtgagcgaa gaaggccttc gggttgtaaa gctctgttgc tcggggagag | 420 |
| cggcatgggg agtggaaagc cccatgcgag acggtaccga gtgaggaagc cccggctaac | 480 |
| tacgtgccag cagccgcggt aaaacgtagg gggcgagcgt tgtccggaat cactgggcgt | 540 |
| aaagggtgcg taggcggtcg agcaagtctg gagtgaaagt ccatggctca accatgggat | 600 |
| ggctctggaa actgcttgac ttgagtgctg gagaggcaag gggaattcca cgtgtagcgg | 660 |
| tgaaatgcgt agagatgtgg aggaatacca gtggcgaagg cgccttgctg gacagtgact | 720 |
| gacgctgagg cacgaaagcg tggggagcaa acaggattag ataccctggt agtccacgcc | 780 |
| gtaaacgatg agtgctaggt gttgggggga cacacccag tgccgaagga aacccaataa | 840 |

```
gcactccgcc tggggagtac ggtcgcaaga ctgaaactca aaggaattga cgggggcccg      900
cacaagcagt ggagcatgtg gtttaattcg aagcaacgcg aagaacctta ccagggcttg      960
acatccctct gacgggtgca gagatgcacc ttcccttcgg ggcagaggag acaggtggtg     1020
catggttgtc gtcagctcgt gtcgtgagat gtttgggttca gtcccgcaac gagcgcaacc    1080
cttgacctgt gttaccagcg cgntanggcg gggactcaca ggtgactgcc ggcgtaagtc    1140
ggaggaaggc ggggatgacg tcaaatcatc atgcccctga tgtcctgggc tacacacgtg     1200
ctacaatggg cggtacaaag ggaggcgaag ccgcgaggcg gagcgaaacc caaaaagccg     1260
ctcgtagttc ggattgcagg ctgcaactcg cctgcatgaa gccggaattg ctagtaatcg     1320
cggatcagca tgccgcggtg aatacgttcc cgggccttgt acacaccgcc cgtcacacca     1380
cgagagtcgg caacacccga agtcggtgag gtaaccccga aaggggagcc agccgccgaa    1440
ggtggggtcg atgattgggg tgaagtcgta acaaggtagc cgtaccggaa ggtgc         1495
```